(12) United States Patent
Koo et al.

(10) Patent No.: US 6,933,496 B2
(45) Date of Patent: Aug. 23, 2005

(54) ION MOBILITY SENSOR

(75) Inventors: Jackson C. Koo, San Ramon, CA (US); Conrad M. Yu, Antioch, CA (US)

(73) Assignee: The Regents of the University of California, Oakland, CA (US)

(*) Notice: Subject to any disclaimer, the term of this patent is extended or adjusted under 35 U.S.C. 154(b) by 252 days.

(21) Appl. No.: 09/883,665

(22) Filed: Jun. 18, 2001

(65) Prior Publication Data

US 2002/0000811 A1 Jan. 3, 2002

Related U.S. Application Data

(60) Provisional application No. 60/213,679, filed on Jun. 23, 2000.

(51) Int. Cl.[7] .............................. B01D 59/44; H01J 49/00
(52) U.S. Cl. ........................ 250/287; 250/282; 250/288
(58) Field of Search ................................ 250/287, 282, 250/288; 73/23.35, 23.4, 31.03, 31.05; 324/464, 71.1, 627

(56) References Cited

U.S. PATENT DOCUMENTS

| 3,114,877 | A | * | 12/1963 | Dunham | 324/71.1 |
|---|---|---|---|---|---|
| 3,449,667 | A | * | 6/1969 | Gourdine | 324/71.1 |
| 4,238,678 | A | * | 12/1980 | Castleman et al. | 250/381 |
| 4,633,083 | A |  | 12/1986 | Knorr et al. | 250/282 |
| 4,883,958 | A | * | 11/1989 | Vestal | 250/288 |
| 5,371,364 | A | * | 12/1994 | Davies et al. | 250/287 |
| 5,574,277 | A |  | 11/1996 | Taylor | 250/281 |
| 5,736,739 | A |  | 4/1998 | Uber et al. | 250/287 |
| 5,811,059 | A |  | 9/1998 | Genovese et al. | 422/89 |
| 5,955,886 | A | * | 9/1999 | Cohen et al. | 324/464 |

FOREIGN PATENT DOCUMENTS

WO    WO 99/41601    8/1999    ........... G01N/30/02

* cited by examiner

*Primary Examiner*—Hai Pham
*Assistant Examiner*—Lam Nguyen
(74) *Attorney, Agent, or Firm*—James S. Tak; Alan H. Thompson; Eddie E. Scott

(57) ABSTRACT

An ion mobility sensor which can detect both ion and molecules simultaneously. Thus, one can measure the relative arrival times between various ions and molecules. Different ions have different mobility in air, and the ion sensor enables measurement of ion mobility, from which one can identify the various ions and molecules. The ion mobility sensor which utilizes a pair of glow discharge devices may be designed for coupling with an existing gas chromatograph, where various gas molecules are already separated, but numbers of each kind of molecules are relatively small, and in such cases a conventional ion mobility sensor cannot be utilized.

8 Claims, 1 Drawing Sheet

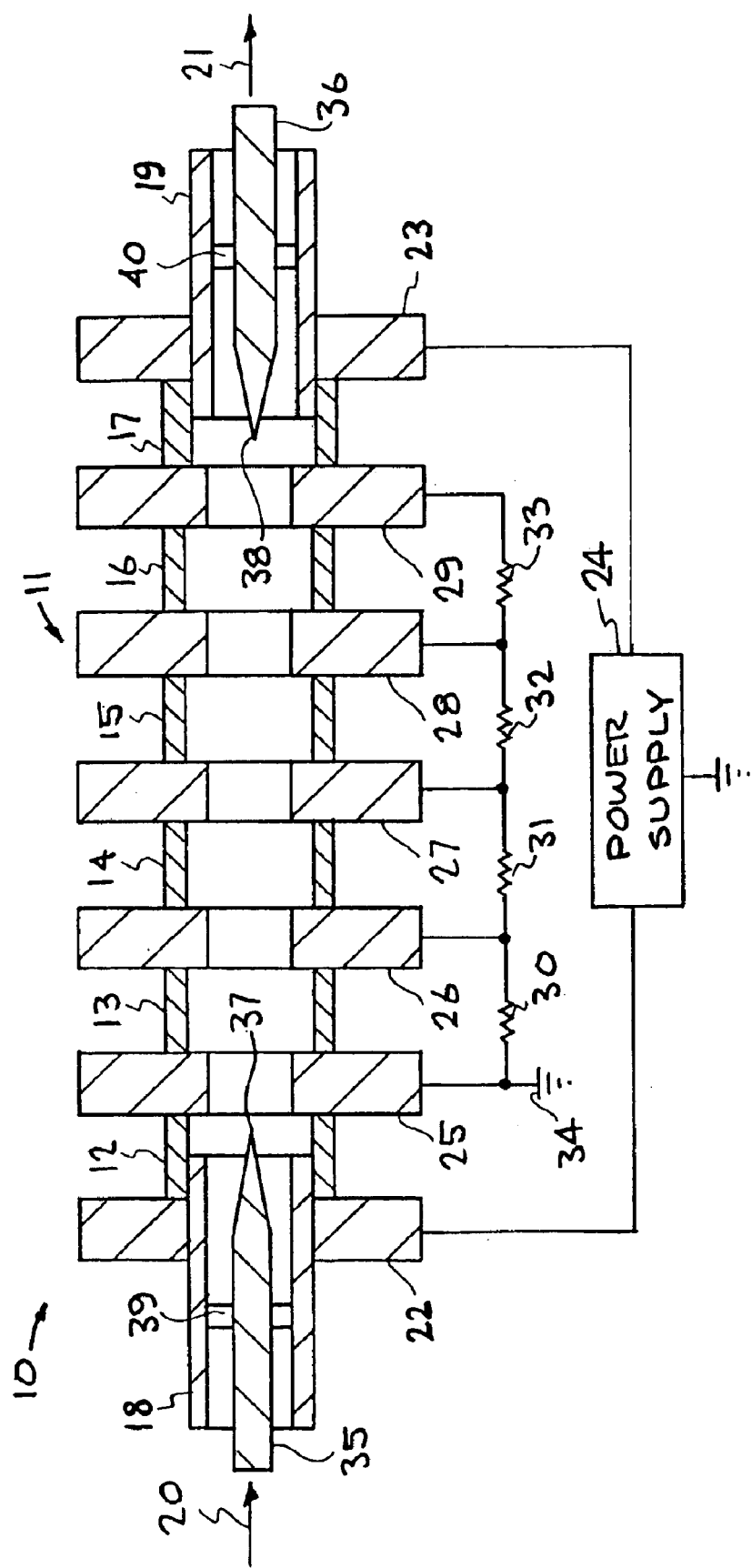

ION MOBILITY SENSOR

RELATED APPLICATION

This application relates to U.S. Provisional Application No. 60/213,679 filed Jun. 23, 2000, and claims priority thereof.

The United States Government has rights in this invention pursuant to Contract No. W-7405-ENG-48 between the United States Department of Energy and the University of California for the operation of Lawrence Livermore National Laboratory.

BACKGROUND OF THE INVENTION

Ion mobility sensors and gas chromatograph/ion mobility sensor coupled systems are known. And ion mobility sensor is used to measure or indirectly derive the speed of ionic molecules under an electrical field in air (the mobility of ions in air). Different molecular ions have different mobility. Therefore, one can determine different molecules with this measurement. In the conventionally known GC/IMS coupled systems macro size separation columns and large gas flow rates are used and selectivity of the gas chromatograph and sensitivity of the ion mobility sensor are compromised. To avoid using a large tank of carrier gas, the conventional systems use a recirculation pump and a repetitive sample concentration unit. For a sample with parts per million impurity, ion current calculated current calculation is in the order of femto amperes. In other words, it is impossible to employ a conventional ion mobility sensor in coupling with the had-held gas chromatograph to be useful. The prior art gas chromatograph/ion mobility sensor coupled systems are exemplified by U.S. Pat. No. 4,633,083 issued Dec. 30, 1986; U.S. Pat. No. 5,574,277 issued Nov. 12, 1996, U.S. Pat. No. 5,736,739 issued Apr. 7, 1998; and U.S. Pat. No. 5,811,059 issued Sep. 22, 1998, and International Application WO 99/41601 published Aug. 19, 1999.

The present invention provides a solution to the above-referenced problems of the GC/IMS coupled systems, by employing a detector which can detect both ions and molecules simultaneously, and the IMS of this invention can detect and measure the relative arrival times between various ions and molecules. The IMS of this invention utilizes a pair of glow discharge devices, one as an ionizer and the other as an ion and molecule detector. The glow discharge devices of this invention are constructed similar to the glow discharge device described and claimed an copending application Ser. No. 09/464,668, filed Dec. 15, 1999, entitled "Glow Discharge Detector", assigned to the same assignee.

SUMMARY OF THE INVENTION

It is an object of the present invention to provide an ion mobility sensor.

A further object of the invention is to provide an ion mobility sensor capable of coupling with gas chromatographs having sample size of about one micro-liter.

A further object of the invention is to provide an ion mobility sensor which can simultaneously detect both molecules and ions with high sensitivity.

Another object of the invention is to provide an ion mobility sensor utilizing a pair of spaced glow discharge device.

Another object of the invention is to provide an ion mobility sensor utilizing a first glow discharge device as an ionizer and a second glow discharge device as an ion and molecule detector.

Another object of the invention is to provide a gas chromatograph/ion mobility detector coupled system, wherein the ion mobility detector is located at an end of an ordinary drift tube, installed behind the separation column of the gas chromatograph, such that the total amount of sample gases can be used in the measurement of the relative ion mobility of various molecules.

Another object of the invention is to provide an ion mobility sensor which can be readily modified in effective length by the selective control of a series of resistive components.

Other objects and advantages of the present invention will become apparent from the following description and accompanying drawing. The present invention is directed to an ion mobility sensor. Since different ions have different mobility in air, the mobility of the different ions can be measured, and from such measurements, one can identify the various ions or molecules. The ion mobility sensor of this invention is particularly designed for coupling with existing gas chromatographs, where various molecules are already separated, but numbers of each kind of molecules are relatively small. By employing a detector which can detect both ions and molecules simultaneously, the ion mobility detector of this invention can detect and measure the relative arrive times between various ions and molecules. By using the sensor of this inventor, one can avoid the usage of high-speed gates and increase the detection sensitivity by detecting the total amount of available molecules.

BRIEF DESCRIPTION OF THE DRAWINGS

The accompanying drawings, which is incorporated into and forms a part of the disclosure, illustrates an embodiment of the invention and, together with the description, serve to explain the principles of the invention.

The single FIGURE illustrates an embodiment of an ion mobility sensor made in accordance with the present invention.

DETAILED DESCRIPTION OF THE INVENTION

The present invention involves an ion mobility sensor which is particularly adapted for coupling with existing gas chromatographs, where various gas molecules are already separated, but numbers of each kind of molecule are relatively small. By use of the invention which employs a detector or sensor which can detect both ions and molecules simultaneously, the ion mobility sensor of this invention can detect and measure the relative times between various ions and molecules. By using this invention one can avoid the usage of high speed gate and increase the detection sensitivity by detecting the total amount of available molecules. Since different ions have different mobility in air the invention enables measurement of ion mobility, from which one can identify the various ion or molecules.

The present invention utilizes glow discharge devices, similar to those of above-referenced application Ser. No. 09/464,668. The sample size of a hand-held gas chromatograph, coupled to the sensor of this invention, is about one micro-liter with the detected signal duration being on the order of one second. The ionization percentage in a glow discharge has been measured at one part per million. For a sample with parts per million impurity, ion current calculated is in the order of femto amperes. Thus, it is impossible to employ a conventional ion mobility sensor in coupling with a hand-held gas chromatograph utilizing a sample size of about one micro-liter. By employing a detector which utilizes a pair of spaced glow discharge devices, one acting as an ionizer and another as a ion and molecule detector, located a the end of an ordinary drift tube installed behind the separation column of a hand held small volume gas chromatograph, the total amount of sample gases can be used in the measurement of the relative ion mobility of various molecules.

Referring now to the drawing, the single figure illustrates an embodiment of the ion mobility sensor of this invention which incorporates two glow discharge devices. The sensor, generally indicated at 10, includes a housing generally indicated at 11 having sections 12, 13, 14, 15, 16 and 17, with a glow discharge ionizer 18 mounted to housing section 12 and a glow discharge ion and molecule detector 19 mounted to housing section 17. Gas, indicated at arrow 20 passes into the sensor 10 via ionizer 18 and is discharged, as indicated at arrow 21 via detector 19. A conductive member 22 is mounted about ionizer 18 and in contact with housing section 12, while as conductive member 23 is mounted about detector 19 and in contact with housing section 17. Conductive members 22 and 23 are operatively connected to a positive and negative side of a power supply 24, which may be a 1500V source. Located intermediate housing sections 12–17 are a plurality of conductive members 25, 26, 27, 28 and 29 having central openings and having resistors 30, 31, 32 and 33 operatively mounted therebetween, with conductive members 25–29 being connected electrically to ground 34. Each of glow discharge devices 18 and 19 include coaxially mounted tubes 35 and 36 in each of which a pointed member or pin 37 and 38 is coaxially mounted by tubes 35 and 36 being pinched as indicated at 39 and 40, or by separate support members, such that there is minimal blockage of gas flow through the sensor 10. As pointed out above, the glow discharge devices 18 and 19 may be constructed similar to those of above referenced application Ser. No. 09/464,668.

This Ion Mobility Spectrometer is designed to be used with the portable Gas Chromatograph (G.C.). It is installed right after the separation column of the portable G.C. The sample volume in the portable GC is about 6 to 10 micron liters. The duration of the sample signal is about one second. In another work, the carrier gas flow rate is about 6 to 10 micro-liters per second. The samples are first separated by the G.C. separation column into many sample plugs through different sample retention times. As each separated sample gas plug flows through this ion mobility spectrometer, it is first ionized through the first glow discharge ionizer. For parts per million samples, there are only about hundred thousand sample ions. These sample ions are accelerated or decelerated depending upon the direction of the electric field in the drift tube. These molecular ions are therefore further separated from their molecules to form their own sample ion plug. The separated sample ion plug together with the sample molecule plug are then measured by the second glow discharge detector. The separation time t between the molecules and its ion is measured. The length of the drift tube L is known. The ion velocity v can be calculated (L/t). The electric field E in the drift tube is known. This particular ion's mobility can also be calculated (Let). In the practical case, the value L/I is measured with samples with known mobility and becomes a system constant for all sample molecules. In this ion mobility spectrometer, there is no electronic gate and no additional counter air flow. Therefor, there is no additional signals to confuse the results.

By way of example the housing sections 12–17 may have an internal diameter of 36 mil and 50 mil and be constructed of glass with, conductive members 22, 23 and 25–29 constructed of tungsten or brass or platinum (white gold). The tubes 35 and 36 constructed of stainless steel and pins 37 and 38 constructed of tungsten or platinum (white gold) with an external diameter of 10 mil to 20 mil.

It has thus been shown that the present invention provides an ion mobility sensor, which includes a pair of spaced glow discharge device and enables detection of both ions and molecules simultaneously. The ion mobility sensor of this invention can detect and measure the relative arrival times between various ion and molecules. This sensor avoids the usage of a high speed gate and increases the detection sensitivity by detecting the total amount of available molecules. The invention has particular application for sensitive two dimensional gas chromatographic systems.

While a particular embodiment of the invention has been illustrated and described along with materials and parameters, to exemplify and teach the principles of the invention, such are not intended to be limiting. Modifications and changes may become apparent to those skilled in the art, and it is intended that the invention be limited only by the scope of the appended claims.

What is claimed is:

1. An ion mobility sensor for simultaneously detecting both ion and molecules, including: a hollow housing;

a glow discharge ionizer mounted to one end of said hollow housing, wherein said glow discharge ionizer includes a hollow tube and a pointed member coaxially mounted in said hollow tube;

a glow discharge detector mounted to an opposite end of said hollow housing, wherein said glow discharge detector includes a hollow tube and a pointed member coaxially mounted in said hollow tube;

said hollow tube of each of said glow discharge ionizer and said glow discharge detector is mounted in opposite ends of said hollow housing, and said glow discharge ionizer and said glow discharge detector are coaxially mounted in said housing and are coaxially aligned one with another; and a pair of conductive members mounted around said hollow tubes of said ionizer and said detector, in contact with opposite ends of said hollow housing, and operatively connected to a power supply.

2. The ion mobility sensor of claim 1, additionally including a plurality of conductive members mounted in spaced relation along a length of said hollow housing, and electrically connected to ground via a plurality of resistors.

3. The ion mobility sensor of claim 2, wherein each one of said plurality of resistors in mounted intermediate an adjacent pair of said plurality of conductive members.

4. The ion mobility sensor of claim 3, wherein said hollow housing is composed of a plurality of sections, and wherein said plurality of conductive members are each mounted intermediate adjacent pairs of said plurality of housing sections.

5. The ion mobility sensor of claim 4, wherein each of said plurality of conductive members has an opening therethrough.

6. The ion mobility sensor of claim 5, wherein each opening in said plurality of conductive members is in alignment with said pointed member of each of said glow discharge ionizer and said glow discharge detector.

7. The ion mobility sensor of claim 6, wherein said pointed members of said glow discharge ionizer and said glow discharge detector are mounted such that points of said pointed member are aligned with and directed toward each other.

8. The ion mobility sensor of claim 7, in combination with a chromatograph.

* * * * *